US 6,568,390 B2
(12) United States Patent
Nichols et al.

(10) Patent No.: US 6,568,390 B2
(45) Date of Patent: May 27, 2003

(54) DUAL CAPILLARY FLUID VAPORIZING DEVICE

(75) Inventors: Walter A. Nichols, Chesterfield, VA (US); Kenneth A. Cox, Midlothian, VA (US); Tung Tien Nguyen, Midlothian, VA (US)

(73) Assignee: Chrysalis Technologies Incorporated, Richmond, VA (US)

( * ) Notice: Subject to any disclaimer, the term of this patent is extended or adjusted under 35 U.S.C. 154(b) by 69 days.

(21) Appl. No.: 09/956,966

(22) Filed: Sep. 21, 2001

(65) Prior Publication Data

US 2003/0056790 A1 Mar. 27, 2003

(51) Int. Cl.[7] .......................... A61M 15/00; H05B 3/02; H05B 1/02
(52) U.S. Cl. ............................ 128/203.16; 128/200.14; 219/486; 219/483; 219/497
(58) Field of Search ................. 128/200.14, 200.19, 128/200.21, 200.22, 200.23, 201.13, 203.16, 203.17, 203.23, 203.24, 203.26, 203.27, 204.17; 239/128, 134, 135; 219/486, 483, 497

(56) References Cited

U.S. PATENT DOCUMENTS 2,896,856 A    7/1959   Kravits (List continued on next page.)

FOREIGN PATENT DOCUMENTS

| BE | 354004 A   | 9/1928  |
|----|------------|---------|
| BE | 354094 A   | 9/1928  |
| DE | 1036470 B1 | 8/1958  |
| EP | 0358114 A  | 3/1990  |
| EP | 0642802 A2 | 5/1996  |
| FR | 667979 A   | 10/1929 |
| HU | 168128 B   | 11/1977 |
| HU | 216121 B   | 3/1991  |
| HU | 207457 A   | 4/1993  |
| HU | P953409    | 6/1994  |
| WO | 94/09842 A | 5/1994  |
| WO | 98/17131   | 4/1998  |

OTHER PUBLICATIONS

Barry, P.W. et al. "In Vitro Comparison of the Amount of Salbutamol Available for Inhalation From Different Formulations Used with Different Spacer Devices" Eur Respir J 1997; 10: 1345–1348.

(List continued on next page.)

Primary Examiner—Weilun Lo
Assistant Examiner—Teena Mitchell
(74) Attorney, Agent, or Firm—Burns, Doane, Swecker & Mathis, LLP

(57) ABSTRACT

A fluid vaporizing device useful for vaporizing fluid into an aerosol and includes first and second capillary tubes connected electrically in series by providing separate electrodes at the inlet ends of each capillary tube, and connecting the outlet ends of the capillary tubes by an electrical connection that connects the outlet ends both electrically and thermally. The capillary tubes are heated by the flow of electricity therethrough, and liquid flowing through the tubes is vaporized. The outlet ends of the capillary tubes are easily maintained at a temperature for optimizing aerosol generation since there is minimal heat loss through the connection connecting the outlet ends.

20 Claims, 1 Drawing Sheet

U.S. PATENT DOCUMENTS

| | | |
|---|---|---|
| 3,084,698 A | 4/1963 | Smith |
| 3,157,179 A | 11/1964 | Paullus et al. |
| 3,162,324 A | 12/1964 | Houser |
| 3,431,393 A | 3/1969 | Katsuda |
| 3,486,663 A | 12/1969 | Humphrey |
| 3,658,059 A | 4/1972 | Steil |
| 3,716,416 A | 2/1973 | Adlhart et al. |
| 3,750,961 A | 8/1973 | Franz |
| 3,847,304 A | 11/1974 | Cohen |
| 3,859,398 A | 1/1975 | Havstad |
| 3,902,635 A | 9/1975 | Jinotti |
| 3,903,883 A | 9/1975 | Pecina et al. |
| 3,904,083 A | 9/1975 | Little |
| 3,967,001 A | 6/1976 | Almaula et al. |
| 3,987,941 A | 10/1976 | Blessing |
| 3,993,246 A | 11/1976 | Erb et al. |
| 3,995,371 A | 12/1976 | O'Keefe |
| 4,042,153 A | 8/1977 | Callahan et al. |
| 4,060,082 A | 11/1977 | Lindberg et al. |
| 4,077,542 A | 3/1978 | Petterson |
| 4,161,282 A | 7/1979 | Erb et al. |
| 4,162,501 A | 7/1979 | Mitchell et al. |
| 4,215,708 A | 8/1980 | Bron |
| 4,231,492 A | 11/1980 | Rios |
| 4,258,073 A | 3/1981 | Payne |
| 4,259,409 A | 3/1981 | Arnold |
| 4,261,356 A | 4/1981 | Turner et al. |
| 4,289,003 A | 9/1981 | Yang |
| 4,291,838 A | 9/1981 | Williams |
| 4,303,083 A | 12/1981 | Burruss, Jr. |
| 4,383,171 A | 5/1983 | Sinha et al. |
| 4,391,308 A | 7/1983 | Steiner |
| 4,395,303 A | 7/1983 | Weir |
| 4,433,797 A | 2/1984 | Galia |
| 4,471,892 A | 9/1984 | Coleman |
| 4,512,341 A | 4/1985 | Lester |
| 4,575,609 A | 3/1986 | Fassel et al. |
| 4,627,432 A | 12/1986 | Newell et al. |
| 4,649,911 A | 3/1987 | Knight et al. |
| 4,682,010 A | 7/1987 | Drapeau et al. |
| 4,695,625 A | 9/1987 | Macdonald |
| 4,700,657 A | 10/1987 | Butland |
| 4,730,111 A | 3/1988 | Vestal et al. |
| 4,735,217 A | 4/1988 | Gerth et al. |
| 4,744,932 A | 5/1988 | Browne |
| 4,749,778 A | 6/1988 | Fukuzawa et al. |
| 4,762,995 A | 8/1988 | Browner et al. |
| 4,776,515 A | 10/1988 | Michalchik |
| 4,790,305 A | 12/1988 | Zoltan et al. |
| 4,811,731 A | 3/1989 | Newell et al. |
| 4,819,625 A | 4/1989 | Howe |
| 4,819,834 A | 4/1989 | Thiel |
| 4,829,996 A | 5/1989 | Noakes et al. |
| 4,837,260 A | 6/1989 | Sato et al. |
| 4,848,374 A | 7/1989 | Chard et al. |
| 4,871,115 A | 10/1989 | Hessey |
| 4,871,623 A | 10/1989 | Hoopman et al. |
| 4,877,989 A | 10/1989 | Drews et al. |
| 4,911,157 A | 3/1990 | Miller |
| 4,917,119 A * | 4/1990 | Potter et al. ................. 131/273 |
| 4,922,901 A | 5/1990 | Brooks et al. |
| 4,926,852 A | 5/1990 | Zoltan et al. |
| 4,935,624 A | 6/1990 | Henion et al. |
| 4,941,483 A | 7/1990 | Ridings et al. |
| 4,947,875 A | 8/1990 | Brooks et al. |
| 4,974,754 A | 12/1990 | Wirz |
| 4,982,097 A | 1/1991 | Slivon et al. |
| 4,992,206 A | 2/1991 | Waldrop |
| 5,021,802 A | 6/1991 | Allred |
| 5,044,565 A | 9/1991 | Alexander |
| 5,056,511 A | 10/1991 | Ronge |
| 5,060,671 A | 10/1991 | Counts et al. |
| 5,063,921 A | 11/1991 | Howe |
| 5,096,092 A | 3/1992 | Devine |
| 5,125,441 A | 6/1992 | Mette |
| 5,133,343 A | 7/1992 | Johnson, IV et al. |
| 5,134,993 A | 8/1992 | van der Linden et al. |
| 5,135,009 A | 8/1992 | Müller et al. |
| 5,144,962 A | 9/1992 | Counts et al. |
| 5,151,827 A | 9/1992 | Ven et al. |
| 5,178,305 A | 1/1993 | Keller |
| 5,184,776 A | 2/1993 | Minier |
| 5,217,004 A | 6/1993 | Blasnik et al. |
| 5,226,441 A | 7/1993 | Dunmire et al. |
| 5,228,444 A | 7/1993 | Burch |
| 5,230,445 A | 7/1993 | Rusnak |
| 5,231,983 A | 8/1993 | Matson et al. |
| 5,259,370 A | 11/1993 | Howe |
| 5,290,540 A | 3/1994 | Prince et al. |
| 5,298,744 A | 3/1994 | Mimura et al. |
| 5,299,565 A | 4/1994 | Brown |
| 5,322,057 A | 6/1994 | Raabe et al. |
| 5,327,915 A | 7/1994 | Porenski et al. |
| 5,342,180 A | 8/1994 | Daoud |
| 5,342,645 A | 8/1994 | Eisele et al. |
| 5,349,946 A | 9/1994 | McComb |
| 5,395,445 A | 3/1995 | Bohanan |
| 5,421,489 A | 6/1995 | Holzner, Sr. et al. |
| 5,454,059 A * | 9/1995 | Regehr ....................... 392/334 |
| 5,462,597 A | 10/1995 | Jubran |
| 5,474,059 A | 12/1995 | Cooper |
| 5,509,557 A | 4/1996 | Jimarez et al. |
| 5,515,842 A | 5/1996 | Ramseyer et al. |
| 5,522,385 A | 6/1996 | Lloyd et al. |
| 5,556,964 A | 9/1996 | Hofstraat et al. |
| 5,564,442 A | 10/1996 | MacDonald et al. |
| 5,565,677 A | 10/1996 | Wexler |
| 5,575,929 A | 11/1996 | Yu et al. |
| 5,585,045 A | 12/1996 | Heinonen et al. |
| 5,617,844 A | 4/1997 | King |
| 5,642,728 A | 7/1997 | Andersson et al. |
| 5,666,977 A * | 9/1997 | Higgins et al. ............. 131/194 |
| 5,674,860 A | 10/1997 | Carling et al. |
| 5,682,874 A | 11/1997 | Grabenkort et al. |
| 5,730,158 A | 3/1998 | Collins et al. |
| 5,743,251 A | 4/1998 | Howell et al. |
| 5,756,995 A | 5/1998 | Maswadeh et al. |
| 5,765,724 A | 6/1998 | Amberg et al. |
| 5,809,210 A * | 9/1998 | Moore et al. ............... 392/402 |
| 5,823,178 A | 10/1998 | Lloyd et al. |
| 5,839,430 A | 11/1998 | Cama |
| 5,855,202 A | 1/1999 | Andrade |
| 5,856,671 A | 1/1999 | Henion et al. |
| 5,863,652 A | 1/1999 | Matsumura et al. |
| 5,865,185 A * | 2/1999 | Collins et al. ............. 131/194 |
| 5,869,133 A | 2/1999 | Anthony et al. |
| 5,872,010 A | 2/1999 | Karger et al. |
| 5,878,752 A | 3/1999 | Adams et al. |
| 5,881,714 A | 3/1999 | Yokoi et al. |
| 5,906,202 A | 5/1999 | Schuster et al. |
| 5,914,122 A | 6/1999 | Otterbeck et al. |
| 5,932,249 A | 8/1999 | Gruber et al. |
| 5,932,315 A | 8/1999 | Lum et al. |
| 5,934,272 A | 8/1999 | Lloyd et al. |
| 5,934,273 A | 8/1999 | Andersson et al. |
| 5,944,025 A | 8/1999 | Cook et al. |
| 5,954,979 A | 9/1999 | Counts et al. |
| 5,957,124 A | 9/1999 | Lloyd et al. |
| 5,970,973 A | 10/1999 | Gonda et al. |
| 5,970,974 A | 10/1999 | Van Der Linden et al. |
| 5,978,548 A | 11/1999 | Holmstrand et al. |

| | | |
|---|---|---|
| 5,993,633 A | 11/1999 | Smith et al. |
| 6,014,970 A | 1/2000 | Ivri et al. |
| 6,053,176 A | 4/2000 | Adams et al. |
| 6,054,032 A | 4/2000 | Haddad et al. |
| 6,069,214 A | 5/2000 | McCormick et al. |
| 6,069,219 A | 5/2000 | McCormick et al. |
| 6,070,575 A | 6/2000 | Gonda et al. |
| 6,071,428 A | 6/2000 | Franks et al. |
| 6,071,554 A | 6/2000 | Isomura et al. |
| 6,076,522 A | 6/2000 | Dwivedi et al. |
| 6,077,543 A | 6/2000 | Gordon et al. |
| 6,080,721 A | 6/2000 | Patton |
| 6,085,740 A | 7/2000 | Ivri et al. |
| 6,085,753 A | 7/2000 | Gonda et al. |
| 6,089,228 A | 7/2000 | Smith et al. |
| 6,095,134 A * | 8/2000 | Sievers et al. ......... 128/200.14 |
| 6,095,153 A | 8/2000 | Kessler et al. |
| 6,098,615 A | 8/2000 | Lloyd et al. |
| 6,098,620 A | 8/2000 | Lloyd et al. |
| 6,103,270 A | 8/2000 | Johnson et al. |
| 6,116,516 A | 9/2000 | Gañán-Calvo |
| 6,116,893 A | 9/2000 | Peach |
| 6,119,953 A | 9/2000 | Gañán-Calvo et al. |
| 6,123,068 A | 9/2000 | Lloyd et al. |
| 6,123,936 A | 9/2000 | Platz et al. |
| 6,131,567 A | 10/2000 | Gonda et al. |
| 6,131,570 A | 10/2000 | Schuster et al. |
| 6,136,346 A | 10/2000 | Eljamal et al. |
| 6,138,668 A | 10/2000 | Patton et al. |
| 6,155,268 A | 12/2000 | Takeuchi |
| 6,158,431 A | 12/2000 | Poole |
| 6,158,676 A | 12/2000 | Hughes |
| 6,159,188 A | 12/2000 | Laibovitz et al. |
| 6,164,630 A | 12/2000 | Birdsell et al. |
| 6,165,463 A | 12/2000 | Platz et al. |
| 6,167,880 B1 | 1/2001 | Gonda et al. |
| 6,174,469 B1 | 1/2001 | Gañán-Calvo |
| 6,182,712 B1 | 2/2001 | Stout et al. |
| 6,187,214 B1 | 2/2001 | Gañán-Calvo |
| 6,187,344 B1 | 2/2001 | Eljamal et al. |
| 6,189,803 B1 | 2/2001 | Gañán-Calvo |
| 6,192,882 B1 | 2/2001 | Gonda |
| 6,197,835 B1 | 3/2001 | Gañán-Calvo |
| 6,205,999 B1 | 3/2001 | Ivri et al. |
| 6,206,242 B1 | 3/2001 | Amberg et al. |
| 6,207,135 B1 | 3/2001 | Rössling et al. |
| 6,223,746 B1 | 5/2001 | Jewett et al. |
| 6,230,706 B1 | 5/2001 | Gonda et al. |
| 6,231,851 B1 | 5/2001 | Platz et al. |
| 6,234,167 B1 | 5/2001 | Cox et al. |
| 6,234,402 B1 | 5/2001 | Gañán-Calvo |
| 6,235,177 B1 | 5/2001 | Borland et al. |
| 6,250,298 B1 | 6/2001 | Gonda et al. |
| 6,257,233 B1 | 7/2001 | Burr et al. |
| 6,258,341 B1 | 7/2001 | Foster et al. |
| 6,263,872 B1 | 7/2001 | Schuster et al. |
| 6,267,155 B1 | 7/2001 | Parks et al. |
| 6,275,650 B1 | 8/2001 | Lambert |
| 6,276,347 B1 | 8/2001 | Hunt |
| 6,284,525 B1 | 9/2001 | Mathies et al. |
| 6,288,360 B1 | 9/2001 | Beste |
| 6,290,685 B1 | 9/2001 | Insley et al. |
| 6,294,204 B1 | 9/2001 | Rössling et al. |
| 6,295,986 B1 | 10/2001 | Patel et al. |
| 6,318,361 B1 | 11/2001 | Sosiak |
| 6,443,146 B1 * | 9/2002 | Voges ................... 128/200.14 |
| 6,491,233 B2 * | 12/2002 | Nichols ..................... 239/128 |
| 6,501,052 B2 * | 12/2002 | Cox et al. .................. 219/486 |
| 2001/0032647 A1 | 10/2001 | Schuster et al. |

OTHER PUBLICATIONS

Byron, Peter R. Ph.D., Chairman, "Recommendations of the USP Advisory Panel on Aerosols on the USP General Chapters on Aerosols (601) and Uniformity of Dosage Units (905)", Pharmacopeial Forum, vol. 20, No. 3, pp. 7477–7505, May–Jun. 1994 (023).

Hindle, Michael et al., "High Efficiency Aerosol Production Using the Capillary Aerosol Generator" PharmSci 1998; 1: (1: suppl) S211.

Hindle, Michael et al., "High Efficiency Fine Particle Generation Using Novel Condensation Technology", Respiratory Drug Delivery VI (eds Dalby, R.N., Byron, P.R. & Farr, S.J.) Interpharm Press, Buffalo Grove, IL 1998 pp 97–102.

Hou, Shuguang et al. *Solution Stability of Budensonide in Novel Aerosol Formulations* Abstract No. 2582, Solid State Physical Pharmacy, Nov. 17, 1998, p. S–307.

Kousaka, Yasuo et al., "Generation of Aerosol Particles by Boiling of Suspensions", Aerosol Science and Technology, 21:236–240 (1994) (023).

Morén, Folke "Drug Deposition of Pressurized Inhalation Aerosols I. Influence of Actuator Tube Design" AB Draco (Subsidiary of AB Astra, Sweden) Research and Development Laboratories Pack, S–221 01 Lund (Sweden), International Journal of Pharmaceutrics, 1 (1978) 205–212.

Newman, Stephen P. et al. "Deposition of Pressurized Suspension Aerosols Inhaled Through Extension Devices[1–3]" Am Rev Respir Dis 1981; 124:317–320.

Roth, G. et al. High Performance Liquid Chromatographic Determination of Epimers, Impurities, and Content of the Glucocorticoid Budesonide and Preparation of Primary Standard, Journal of Pharmaceutical Sciences, vol. 69, No. 7, pp. 776–770, Jul. 1980.

* cited by examiner

DUAL CAPILLARY FLUID VAPORIZING DEVICE

BACKGROUND OF THE INVENTION

1. Field of the Invention

The present invention relates generally to fluid vaporizing devices such as aerosol generators.

2. Brief Description of the Related Art

Aerosols are useful in a wide variety of applications. For example, it is often desirable to treat respiratory ailments with, or deliver drugs by means of, aerosol sprays of finely divided particles of liquid and/or solid, e.g., powder, medicaments, etc., which are inhaled into a patient's lungs. Aerosols are also used for purposes such as providing desired scents to rooms, distributing insecticides and delivering paint and lubricant.

Various techniques are known for generating aerosols. For example, U.S. Pat. Nos. 4,811,731 and 4,627,432 disclose devices for administering medicaments to patients in which a capsule is pierced by a pin to release a medicament in powder form. A user then inhales the released medicament through an opening in the device. While such devices may be acceptable for use in delivering medicaments in powder form, they are not suited to delivering medicaments in liquid form. The devices are also, of course, not well-suited to delivery of medicaments to persons who might have difficulty in generating a sufficient flow of air through the device to properly inhale the medicaments, such as asthma sufferers. The devices are also not suited for delivery of materials in applications other than medicament delivery.

Another well-known technique for generating an aerosol involves the use of a manually operated pump which draws liquid from a reservoir and forces it through a small nozzle opening to form a fine spray. A disadvantage of such aerosol generators, at least in medicament delivery applications, is the difficulty of properly synchronizing inhalation with pumping. More importantly, however, because such aerosol generators tend to produce particles of large size, their use as inhalers is compromised because large particles tend to not penetrate deeply into the lungs.

One of the more popular techniques for generating an aerosol including liquid or powder particles involves the use of a compressed propellant, often containing a chlorofluoro-carbon (CFC) or methylchloroform, to entrain a material, usually by the Venturi principle. For example, inhalers containing compressed propellants such as compressed gas for entraining a medicament are often operated by depressing a button to release a short charge of the compressed propellant. The propellant entrains the medicament as the propellant flows over a reservoir of the medicament so that the propellant and the medicament can be inhaled by the user.

In propellant-based arrangements, however, a medicament may not be properly delivered to the patient's lungs when it is necessary for the user to time the depression of an actuator such as a button with inhalation. Moreover, aerosols generated by propellant-based arrangements may have particles that are too large to ensure efficient and consistent deep lung penetration. Although propellant-based aerosol generators have wide application for uses such as antiperspirant and deodorant sprays and spray paint, their use is often limited because of the well-known adverse environmental effects of CFC's and methylchloroform, which are among the most popular propellants used in aerosol generators of this type.

In drug delivery applications, it is typically desirable to provide an aerosol having average mass median particle diameters of less than 2 microns to facilitate deep lung penetration. Propellant based aerosol generators are incapable of generating aerosols having average mass median particle diameters less than 2 microns. It is also desirable, in certain drug delivery applications, to deliver medicaments at high flow rates, e.g., above 1 milligram per second. Some aerosol generators suited for drug delivery are incapable of delivering such high flow rates in the 0.2 to 2.0 micron size range.

Commonly owned U.S. Pat. Nos. 5,743,251 and 6,234,167, which are hereby incorporated by reference in their entirety, disclose aerosol generators, along with certain principles of operation and materials used in an aerosol generator, as well as methods of producing an aerosol, and an aerosol.

SUMMARY OF THE INVENTION

The invention provides a dual capillary fluid vaporizing device that includes a fluid source, a power source, and a heater arrangement electrically heated by the power source. The heater arrangement includes first and second capillary tubes, with the capillary tubes having inlet ends in fluid communication with the fluid source and the heater arrangement being operable to vaporize fluid in the capillary tubes. A first electrode supplies electrical current to the first capillary tube such that electrical current passes along at least a portion of the first capillary tube. An electrical connection connects the capillary tubes such that the electrical current supplied to the first capillary tube passes along at least a portion of the second capillary tube, and a second electrode is electrically connected to the second capillary tube such that the capillary tubes are electrically connected in series to the power source.

The invention also provides a method of vaporizing fluid that includes supplying fluid from the fluid source to first and second capillary tubes, and heating the first and second capillary tubes by passing electrical current from the power source along the first capillary tube, through the electrical connection interconnecting the first and second capillary tubes, and along the second capillary tube, the electrical current being effective to heat the capillary tubes such that the fluid therein is volatilized and exits the capillary tubes as a vapor.

BRIEF DESCRIPTION OF THE DRAWINGS

The invention of the present application will now be described in more detail with reference to preferred embodiments of the apparatus and method, given only by way of example, and with reference to the accompanying drawing, in which.

DESCRIPTION OF THE PREFERRED EMBODIMENTS

Figure 1:
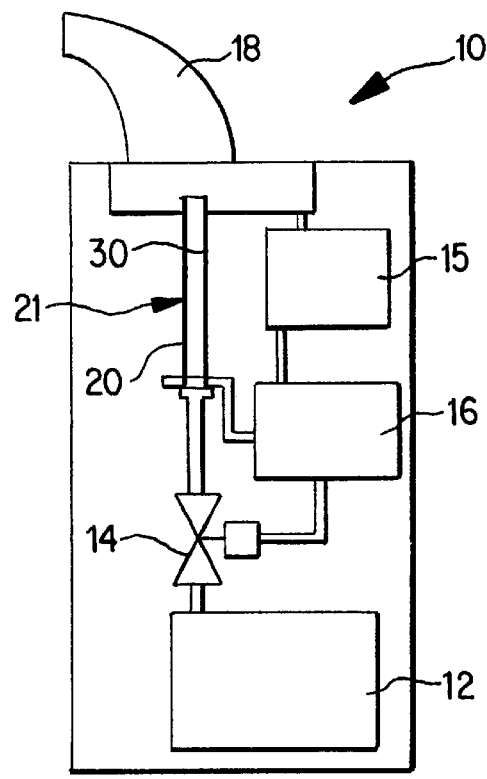
FIG. 1 is an illustration of a fluid vaporizing device according to a preferred embodiment of the invention.
Figure 2:
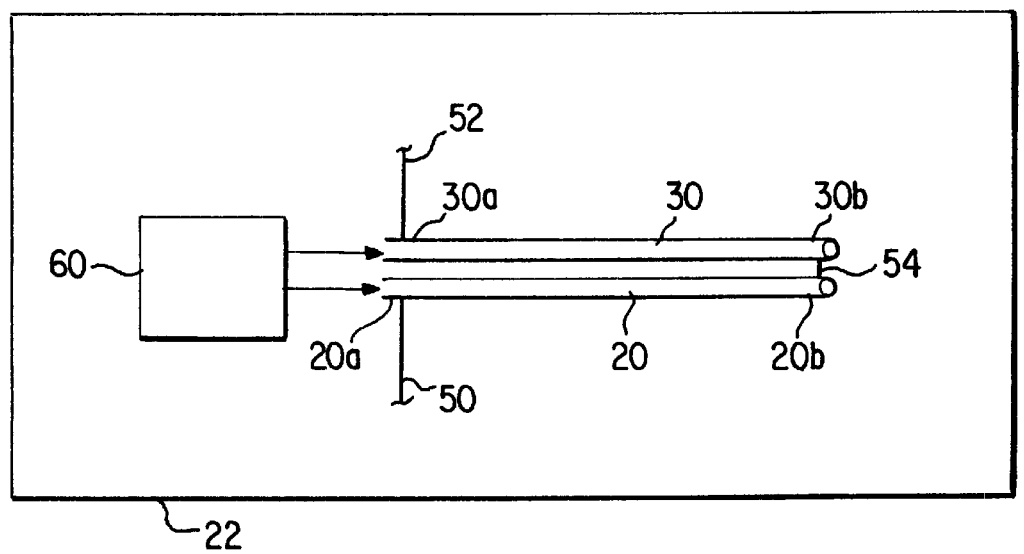
FIG. 2 is a schematic representation of a dual capillary tube portion of the device shown in FIG. 1 according to an embodiment of the invention.

The invention provides a fluid vaporizing device useful for applications including aerosol generation. The device according to an embodiment of the invention includes two capillary tubes which can be heated by passing electrical current therethrough, the tubes being connected electrically in series, and through which fluid flows to be at least partially vaporized and if desired to generate an aerosol. While aerosol generation is one use of the fluid vaporizing device, other uses could include vaporizing other liquids such as fuel. In order to heat the tubes, an electrical current enters the first tube through a first electrode at the inlet end, flows along the tube and through an electrical connection which connects the first tube outlet end to the second tube outlet end, and flows along the second tube from the outlet end to a second electrode at the inlet end of the second tube. Fluid from the same or different sources can be supplied as a pressurized liquid at the inlets to the respective tubes and is converted to a vapor by the input of heat from the flow of electricity through the tubes as the fluid flows through the tubes toward the outlet ends. When used as an aerosol generator, as the vapor exits from the tubes at the respective outlet ends or tips of the capillary tubes, at least some of the vapor condenses to form droplets of aerosol as the vapor enters the surrounding atmosphere.

The capillary tubes can be made entirely from an electrically conductive material, such as stainless steel, so that as a voltage is applied to the tubes, the tubes are heated by the flow of electric current through the tubes, which are electrically connected in series, and the fluid passing through the tubes is vaporized. As an alternative, the tubes could be made from a non-conductive or semi-conductive material, such as glass or silicon, with a resistance heating material such as platinum (Pt). The capillary tubes are connected electrically in series by providing a separate electrode or joint at the outlet end of each tube which electrically connects the outlet ends of the tubes together. The electrical connection at the outlet ends or tips of the capillary tubes also provides a thermal connection, such that the temperature at the tip of the first capillary tube in the direction of the flow of electricity is the same or nearly the same as the temperature at the tip of the second capillary tube. This arrangement minimizes heat loss compared to a single capillary tube arrangement wherein an electrical lead is attached to the outlet end of the capillary tube. The parallel arrangement of the capillary tubes also provides for a very compact structure and allows generation of a greater amount of vaporized material than in the case of a single capillary tube. Of course, the tubes do not need to be arranged in parallel, as long as the outlet end of the second capillary tube in the direction of the flow of electricity is electrically and thermally connected to the outlet end of the first capillary tube. For example, the ends of the tubes could be welded, brazed or soldered together and the tubes angled apart to isolate them electrically from each other.

The coefficient of heat transfer between the tubes and the fluid flowing through the tubes decreases in the direction of flow as the liquid is converted into a vapor. Accordingly, the outlet ends of the capillary tubes are at a higher temperature than the inlet ends. By providing substantially identical capillary tubes, each carrying a substantially identical flow of fluid, the outlet ends of the tubes can be maintained at substantially the same temperature. The connection of the outlet ends of essentially identical capillary tubes carrying substantially the same flow of fluid to be vaporized and optionally aerosolized ensures that there is minimal heat loss at the outlet ends as a result of the electrical connection. If desired, the tubes can be of different diameters and/or lengths and the fluid supplied to the tubes can be the same or different fluids.

The dual capillary aerosol generator according to an embodiment of the invention maintains the temperature at the tips of the capillary tubes sufficiently high for the generation of a quality aerosol without necessitating overheating of the capillary mid-sections. Suitable materials and dimensions can be used for the electrical connection near the tip of the capillary tubes, and the arrangement can optimize the generation of quality aerosol regardless of the fluid or fluid flow rate through the tubes.

One advantage of this invention is that by forming both an electrical and a thermal connection at the tip of a capillary tube with an identical capillary tube, the temperature at the first end of this connection (the temperature of the first capillary tip) is generally substantially matched by the temperature at the second end (the temperature of the second capillary tip). This eliminates the potential for heat loss at the tip due to thermal conduction along the electrical lead, since any temperature gradient has been substantially eliminated. Furthermore, no special effort is needed to design the electrical connection. Finally, the design is independent of fluid flow rate. Because additional energy is not needed in warming an electrical lead, the configuration can be expected to be more efficient, perhaps by 10–20%, than a capillary tube aerosol generator in which a resistance heating electrode at the outlet end of a capillary tube-type aerosol generator is used to generate heat and minimize heat loss at the capillary tip.

The present invention provides an improvement to a single capillary tube arrangement used to vaporize fluid wherein heat loss can occur at an electrical lead nearest the capillary tube exit and cause a dramatic decline in temperature along the capillary toward the tip. To compensate for such heat loss and maintain the tip at a temperature sufficiently high for the generation of a quality aerosol, the capillary midsection may be overheated. This overheating exposes the materials to be aerosolized to unnecessarily high temperatures which can, in some cases, be sufficient to cause thermal degradation of these materials.

FIG. 1 shows an embodiment of a fluid vaporizing device in the form of an aerosol generator 10 in accordance with one embodiment of the invention. As shown, the aerosol generator 10 includes a source 12 of fluid, a valve 14, a heater arrangement 21 comprising dual parallel capillary passages 20, 30, a mouthpiece 18, an optional sensor 15 and a controller 16. The controller 16 includes suitable electrical connections and ancillary equipment such as a battery which cooperates with the controller for operating the valve 14, the sensor 15 and supplying electricity to heat the dual parallel capillary passages 20, 30. In operation, the valve 14 can be opened to allow a desired volume of fluid from the source 12 to enter the passages 20, 30 prior to or subsequent to detection by the sensor 15 of vacuum pressure applied to the mouthpiece 18 by a user attempting to inhale aerosol from the aerosol generator 10. As fluid is supplied to the passages 20, 30, the controller 16 controls the amount of power provided to heat the capillary tubes sufficient to volatilize fluid in the passages 20, 30, i.e., the controller 16 controls the amount of electricity passed through the capillary tubes to heat the fluid to a suitable temperature for volatilizing the fluid therein. The volatilized fluid exits outlets 20b, 30b of the passages 20, 30, and the volatilized fluid forms an aerosol which can be inhaled by a user drawing upon the mouthpiece 18.

The aerosol generator shown in FIG. 1 can be modified to utilize different fluid supply arrangements. For instance, the fluid source can comprise a delivery valve which delivers a predetermined volume of fluid to the passages 20, 30 and/or the passages 20, 30 can include chambers of predetermined size to accommodate a predetermined volume of fluid to be volatilized during an inhalation cycle. In the case where the passages include chambers to accommodate a volume of fluid, the device can include a valve or valves downstream of the chambers for preventing flow of the fluid beyond the chambers during filling thereof. If desired, the chambers can include a preheater arranged to heat fluid in the chambers such that a vapor bubble expands and drives the remaining liquid from the chambers into the passages 20, 30. Details of such a preheater arrangement can be found in commonly owned U.S. application Ser. No. 09/742,395 filed on Dec. 22, 2000, the disclosure of which is hereby incorporated by reference. If desired, the valve(s) could be omitted and the fluid source 12 can include a delivery arrangement such as a syringe pump which supplies a predetermined volume of fluid to the chamber or directly to the passages 20, 30. The heaters can be the walls of the capillary tubes defining passages 20, 30, arranged to volatilize the liquid in passages 20, 30. In the case of manual operations, the sensor 15 can be omitted such as in the case where the aerosol generator 10 is operated manually by a mechanical switch, electrical switch or other suitable technique. Although the aerosol generator 10 illustrated in FIG. 1 is useful for medical uses, the principles of the device can also be used to vaporize other fluids such as fuel, odorants, or the like.

A dual capillary tube aerosol generator according to an embodiment of the invention includes two capillary tubes that are arranged to receive fluid flow from a single fluid source and that are connected electrically in series. A fluid, generally in the form of a pressurized liquid and/or predetermined volume of fluid, enters through the inlets of the two capillary tubes and flows through the tubes to the exit ends or tips of the capillary tubes. The capillary tubes are connected electrically in series by providing separate electrodes at the inlet ends of each capillary tube and by electrically connecting the tip ends of the capillary tubes together with a conductive element such as a copper wire, a metallurgical joint such as a welded portion of the tubes, or the like. The capillary tubes are heated as a result of the electrical current flowing through the tubes, and the liquid entering the inlet ends of each tube is heated within the tubes to form a vapor. As the vapor exits from the tips of the capillary tubes and comes into contact with the surrounding ambient air, the vapor is condensed into tiny droplets that form an aerosol. The electrical connection between the tubes at the tip end also serves as a thermal connection such that the temperature of the first capillary tube tip is substantially the same as the temperature of the second capillary tube tip. If a simple braze or other type of metallurgical connection is used to connect the two capillary tubes at the exit tips, the electrical resistance across the connection is low and the exit may be cooler than the vapor zones within the capillary tubes. In a preferred embodiment of the invention, the electrical resistance of the connection between the capillary tube tips is controlled by geometry and material selection to regulate exit temperature. In arrangements where the tips of the capillary tubes may be connected to further structure and heat may be transferred to the structure, the electrical resistance of the interconnection can be higher per unit length than the capillary tubes so as to balance the heat transfer and maintain the desired tip temperature.

As shown in FIG. 2, a fluid vaporizing device 22 includes a first capillary tube 20 arranged essentially in parallel to a second capillary tube 30, with a fluid from a fluid source 60 passing through both capillary tubes in parallel. The fluid enters the first capillary tube 20 at inlet end 20*a* and the second capillary tube 30 at inlet 30*a*, and exits as a vapor from the tip 20*b* of capillary tube 20 and the tip 30*b* of capillary tube 30. A first electrode 50 is connected near the inlet end 20*a* of capillary tube 20, and a second electrode 52 is connected near the inlet end 30*a* of second capillary tube 30. The tip 20*b* of capillary tube 20 and tip 30*b* of capillary tube 30 are also connected electrically by a conductive element such as a short electrode.

The arrangement shown in FIG. 2 provides for fluid flow in parallel through the capillary tubes and electrical flow in series. The electrical connection 54 at the tip ends of the capillary tubes also provides a thermal connection such that tip 20*b* of capillary tube 20 is maintained at the same temperature as tip 30*b* of capillary tube 30. The electrical flow through the capillary tubes heats up the tubes, with the temperature profiles along the tubes being determined at least in part by the amount of voltage applied across the tubes and the fluid flow rate through the tubes.

A liquid entering at the inlet 20*a* of capillary tube 20 and inlet 30*a* of capillary tube 30 is heated as it passes through the capillary tubes in parallel. Sufficient heat is input to the fluid passing through the tubes to vaporize the fluid and maintain it in a vaporized state as it exits from the tips 20*b* and 30*b* of the capillary tubes. Since the tips 20*b* and 30*b* can be maintained at substantially the same temperature as a result of the electrical and thermal connection 54, there is no potential for heat loss due to thermal conduction along the electrical connection 54, and it is easier to maintain the tips 20*b*, 30*b* at the necessary temperature for generation of a quality aerosol.

The dual capillary tube arrangement is designed to accommodate a variety of liquid flow rates through the capillary tubes, is highly energy efficient and provides a compact arrangement. In inhaler applications, the heating zones of the capillary tubes can be 5 to 40 mm, or more preferably 10 to 25 mm, and the inner diameters of the tubes can be 0.1 to 0.5 mm, or more preferably 0.2 to 0.4 mm. In implementing the capillary heater in an inhaler, the capillary tube arrangement is preferably insulated and/or isolated from ambient air and the vapor emitted from the capillary tubes. For example, a body of insulating material or a metal foil, such as stainless steel foil, could be used to support the capillary tip within a mouthpiece such that the vapor exiting the capillary tubes does not contact the outer surface of the capillary tubes upstream of the metal foil.

While this invention has been illustrated and described in accordance with a preferred embodiment, it is recognized that variations and changes may be made therein without departing from the invention as set forth in the claims.

What is claimed is:

1. A dual capillary fluid vaporizing device comprising:

at least one fluid source;

a power source;

a heater arrangement electrically heated by the power source, the heater arrangement comprising first and second capillary tubes, the capillary tubes having inlet ends in fluid communication with the fluid source and the heater arrangement being operable to vaporize fluid in the capillary tubes;

a first electrode supplying electrical current to the first capillary tube such that electrical current passes along at least a portion of the first capillary tube;

an electrical connection connecting the capillary tubes such that the electrical current supplied to the first capillary tube passes along at least a portion of the second capillary tube; and a second electrode electrically connected to the second capillary tube such that the capillary tubes are electrically connected in series to the power source.

2. The fluid vaporizing device of claim 1, wherein the first and second capillary tubes comprise stainless steel tubes having inner diameters of 0.1 to 0.5 mm.

3. The fluid vaporizing device of claim 1, wherein the first and second capillary tubes are parallel to each other with the outlet ends thereof spaced apart by at least 1 mm.

4. The fluid vaporizing device of claim 1, wherein the fluid vaporizing device comprises an inhaler having a mouthpiece, the capillary tubes having outlets which direct vaporized fluid into the mouthpiece.

5. The fluid vaporizing device of claim 1, wherein the power source comprises a battery, the first electrode being electrically connected to one terminal of the battery and the second electrode being connected to the other terminal of the battery.

6. The fluid vaporizing device of claim 1, wherein the device comprises an inhaler having a controller, a valve and a sensor, the sensor detecting a delivery condition corresponding to delivery of a predetermined volume of aerosol, the controller being programmed to open the valve so as to deliver liquid from the fluid source to the first and second capillary tubes when the delivery condition is sensed by the sensor and to pass electrical current through the first and second capillary tubes to volatilize liquid therein.

7. The fluid vaporizing device of claim 1, wherein the first and second capillary tubes are of the same material, have the same length and have the same internal diameter.

8. The fluid vaporizing device of claim 1, wherein the first and second electrodes are located at least 5 mm from the electrical connection.

9. The fluid vaporizing device of claim 1, wherein the outlet ends of the capillary tubes are exposed to ambient air.

10. The fluid vaporizing device of claim 1, wherein the electrical connection comprises a joint between outer surfaces of the capillary tubes.

11. A method of vaporizing fluid comprising:

supplying fluid from a fluid source to first and second capillary tubes;

heating the first and second capillary tubes by passing electrical current from a power source along the first capillary tube, through an electrical connection interconnecting the first and second capillary tubes, and along the second capillary tube, the electrical current being effective to heat the capillary tubes such that the fluid therein is volatilized and exits the capillary tubes as a vapor.

12. The method of claim 11, wherein the power source comprises a battery and the electric current is direct current which travels in series from the battery, through the first capillary tube, through the electrical connection, through the second capillary tube, and returns to the battery.

13. The method of claim 11, wherein the capillary tubes are of resistance heating material, the fluid being heated as a result of resistance heating the capillary tubes.

14. The method of claim 11, wherein the electrical connection is located at outlet ends of the capillary tubes, the outlet ends being heated to substantially the same temperature during heating of the capillary tubes.

15. The method of claim 11, wherein the capillary tubes are parallel to each other, are of the same material, have the same length and have the same inner diameters.

16. The method of claim 11, wherein the capillary tubes are in fluid communication with the same source of fluid.

17. The method of claim 11, wherein the fluid vaporizing device comprises an inhaler having a mouthpiece, the capillary tubes having outlets in the mouthpiece such that the vapor exiting the outlets condenses into an aerosol within the mouthpiece.

18. The method of claim 17, wherein the inhaler includes a controller, a valve and a sensor, the method including sensing a delivery condition with the sensor, sending a signal to the controller corresponding to the delivery condition, opening the valve for delivery of a predetermined volume of fluid from the fluid source to the first and second capillary tubes, supplying power to the first and second capillary tubes, and closing the valve after a predetermined volume of fluid has been delivered to the first and second capillary tubes.

19. The method of claim 11, wherein the first and second capillary tubes have outlets thereof in close proximity and the vapor exiting the outlets condenses in ambient air.

20. The method of claim 11, wherein the fluid source contains a solution of medicated material and the vapor exiting the capillary tubes forms an aerosol containing the medicated material.

* * * * *